(12) United States Patent  (10) Patent No.: US 8,529,606 B2
Alamin et al.  (45) Date of Patent: Sep. 10, 2013

(54) SURGICAL TETHER APPARATUS AND METHODS OF USE

(75) Inventors: Todd Alamin, Woodside, CA (US);
Colin Cahill, Portola Valley, CA (US);
Louis Fielding, San Carlos, CA (US);
Manish Kothari, San Rafael, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 112 days.

(21) Appl. No.: 12/721,238

(22) Filed: Mar. 10, 2010

(65) Prior Publication Data
US 2010/0234894 A1  Sep. 16, 2010

Related U.S. Application Data

(60) Provisional application No. 61/158,886, filed on Mar. 10, 2009, provisional application No. 61/158,892, filed on Mar. 10, 2009.

(51) Int. Cl.
*A61B 17/88* (2006.01)
*A61B 17/70* (2006.01)

(52) U.S. Cl.
USPC ............... 606/279; 606/248; 606/263

(58) Field of Classification Search
USPC .............. 606/248–249, 279, 257, 263, 74
See application file for complete search history.

(56) References Cited

U.S. PATENT DOCUMENTS

| | | |
|---|---|---|
| 3,648,691 A | 3/1972 | Lumb et al. |
| 4,246,660 A | 1/1981 | Wevers |
| 4,643,178 A | 2/1987 | Nastari et al. |
| 4,708,132 A | 11/1987 | Silvestrini |
| 4,743,260 A | 5/1988 | Burton |
| 4,772,286 A | 9/1988 | Goble et al. |
| 4,776,851 A | 10/1988 | Bruchman et al. |
| 4,794,916 A | 1/1989 | Porterfield et al. |
| 4,870,957 A | 10/1989 | Goble et al. |
| 4,955,910 A | 9/1990 | Bolesky |
| 4,966,600 A | 10/1990 | Songer et al. |
| 5,002,574 A | 3/1991 | May et al. |
| 5,011,484 A | 4/1991 | Breard |

(Continued)

FOREIGN PATENT DOCUMENTS

| | | |
|---|---|---|
| EP | 0 322 334 A1 | 6/1989 |
| EP | 0 743 045 A2 | 11/1996 |

(Continued)

OTHER PUBLICATIONS

International Search Report and Written Opinion of PCT Application No. PCT/US2010/026799, mailed May 7, 2010.

(Continued)

*Primary Examiner* — Eduardo C Robert
*Assistant Examiner* — Julianna N Harvey
(74) *Attorney, Agent, or Firm* — Wilson, Sonsini, Goodrich & Rosati

(57) ABSTRACT

Methods and apparatus for controlling flexion in a spinal segment of a patient include performing a spinal fusion procedure on a pair of adjacent vertebrae in the spinal segment and implanting a constraint device into the patient. Adjusting length or tension in the constraint device allows the constraint device to provide a force a force resistant to flexion of the spinal segment undergoing fusion. The constraint device also modulates loads borne by the spinal segment undergoing fusion or tissue adjacent thereto.

25 Claims, 6 Drawing Sheets

(56) References Cited

U.S. PATENT DOCUMENTS

| | | | |
|---|---|---|---|
| 5,092,866 A | 3/1992 | Breard et al. | |
| 5,108,433 A | 4/1992 | May et al. | |
| 5,116,340 A | 5/1992 | Songer et al. | |
| 5,171,280 A | 12/1992 | Baumgartner | |
| 5,180,393 A | 1/1993 | Commarmond | |
| 5,282,863 A | 2/1994 | Burton | |
| 5,354,917 A | 10/1994 | Sanderson et al. | |
| 5,395,374 A | 3/1995 | Miller et al. | |
| 5,415,658 A | 5/1995 | Kilpela et al. | |
| 5,415,661 A | 5/1995 | Holmes | |
| 5,449,361 A | 9/1995 | Preissman | |
| 5,456,722 A | 10/1995 | McLeod et al. | |
| 5,458,601 A | 10/1995 | Young, Jr. et al. | |
| 5,462,542 A | 10/1995 | Alesi, Jr. | |
| 5,496,318 A | 3/1996 | Howland et al. | |
| 5,540,698 A | 7/1996 | Preissman | |
| 5,562,737 A | 10/1996 | Graf | |
| 5,609,634 A | 3/1997 | Voydeville | |
| 5,628,756 A | 5/1997 | Barker, Jr. et al. | |
| 5,645,084 A | 7/1997 | McKay | |
| 5,645,599 A | 7/1997 | Samani | |
| 5,669,917 A | 9/1997 | Sauer et al. | |
| 5,672,175 A | 9/1997 | Martin | |
| 5,707,379 A | 1/1998 | Fleenor et al. | |
| 5,725,582 A | 3/1998 | Bevan et al. | |
| 5,797,915 A * | 8/1998 | Pierson et al. | 606/74 |
| 5,902,305 A | 5/1999 | Beger et al. | |
| RE36,221 E | 6/1999 | Breard et al. | |
| 5,928,232 A | 7/1999 | Howland et al. | |
| 5,933,452 A | 8/1999 | Eun | |
| 5,935,133 A | 8/1999 | Wagner et al. | |
| 5,964,769 A | 10/1999 | Wagner et al. | |
| 5,989,256 A | 11/1999 | Kuslich et al. | |
| 6,053,921 A | 4/2000 | Wagner et al. | |
| 6,193,721 B1 | 2/2001 | Michelson | |
| 6,224,630 B1 | 5/2001 | Bao et al. | |
| 6,248,106 B1 | 6/2001 | Ferree | |
| 6,283,996 B1 | 9/2001 | Chervitz et al. | |
| 6,296,643 B1 | 10/2001 | Hopf et al. | |
| 6,312,431 B1 * | 11/2001 | Asfora | 606/279 |
| 6,322,279 B1 | 11/2001 | Yamamoto et al. | |
| 6,364,883 B1 | 4/2002 | Santilli | |
| 6,378,289 B1 | 4/2002 | Trudeau et al. | |
| 6,391,030 B1 | 5/2002 | Wagner et al. | |
| 6,395,018 B1 | 5/2002 | Castaneda | |
| 6,436,099 B1 | 8/2002 | Drewry et al. | |
| 6,451,019 B1 | 9/2002 | Zucherman et al. | |
| 6,468,309 B1 | 10/2002 | Lieberman | |
| 6,517,578 B2 | 2/2003 | Hein | |
| 6,558,389 B2 | 5/2003 | Clark et al. | |
| 6,582,433 B2 | 6/2003 | Yun | |
| 6,605,091 B1 | 8/2003 | Iwanski | |
| 6,616,669 B2 | 9/2003 | Ogilvie et al. | |
| 6,626,944 B1 | 9/2003 | Taylor | |
| 6,629,975 B1 | 10/2003 | Kilpela et al. | |
| 6,652,527 B2 | 11/2003 | Zucherman et al. | |
| 6,652,585 B2 | 11/2003 | Lange | |
| 6,656,185 B2 | 12/2003 | Gleason et al. | |
| 6,669,729 B2 | 12/2003 | Chin | |
| 6,682,533 B1 | 1/2004 | Dinsdale et al. | |
| 6,689,140 B2 | 2/2004 | Cohen | |
| 6,689,168 B2 | 2/2004 | Lieberman | |
| 6,695,852 B2 | 2/2004 | Gleason | |
| 6,712,819 B2 | 3/2004 | Zucherman et al. | |
| 6,716,245 B2 | 4/2004 | Pasquet et al. | |
| 6,761,720 B1 | 7/2004 | Senegas | |
| 6,828,357 B1 | 12/2004 | Martin et al. | |
| 6,835,205 B2 | 12/2004 | Atkinson et al. | |
| 6,835,207 B2 | 12/2004 | Zacouto et al. | |
| 6,899,716 B2 | 5/2005 | Cragg | |
| 6,946,000 B2 | 9/2005 | Senegas et al. | |
| 7,029,475 B2 | 4/2006 | Panjabi | |
| 7,087,083 B2 | 8/2006 | Pasquet et al. | |
| 7,101,398 B2 | 9/2006 | Dooris et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,413,576 B2 | 8/2008 | Sybert et al. | |
| 7,445,637 B2 | 11/2008 | Taylor | |
| 7,452,351 B2 * | 11/2008 | Miller et al. | 604/506 |
| 7,458,981 B2 | 12/2008 | Fielding et al. | |
| 7,520,887 B2 | 4/2009 | Maxy et al. | |
| 7,524,324 B2 | 4/2009 | Winslow | |
| 7,553,320 B2 | 6/2009 | Molz, IV et al. | |
| 7,559,951 B2 | 7/2009 | Disilvestro et al. | |
| 7,591,837 B2 | 9/2009 | Goldsmith | |
| 7,608,094 B2 | 10/2009 | Falahee | |
| 7,837,711 B2 | 11/2010 | Bruneau et al. | |
| 2003/0088251 A1 | 5/2003 | Braun et al. | |
| 2004/0116927 A1 | 6/2004 | Graf | |
| 2004/0167520 A1 | 8/2004 | Zucherman et al. | |
| 2004/0172132 A1 | 9/2004 | Ginn | |
| 2004/0243239 A1 * | 12/2004 | Taylor | 623/17.13 |
| 2005/0033435 A1 | 2/2005 | Belliard et al. | |
| 2005/0049708 A1 | 3/2005 | Atkinson et al. | |
| 2005/0123581 A1 | 6/2005 | Ringeisen et al. | |
| 2005/0131405 A1 | 6/2005 | Molz, IV et al. | |
| 2005/0154390 A1 | 7/2005 | Biedermann et al. | |
| 2005/0192581 A1 | 9/2005 | Molz et al. | |
| 2005/0216017 A1 | 9/2005 | Fielding | |
| 2005/0267470 A1 | 12/2005 | McBride | |
| 2005/0267518 A1 | 12/2005 | Wright et al. | |
| 2006/0036324 A1 | 2/2006 | Sachs et al. | |
| 2006/0041259 A1 | 2/2006 | Paul et al. | |
| 2006/0064166 A1 | 3/2006 | Zucherman et al. | |
| 2006/0084976 A1 | 4/2006 | Borgstrom et al. | |
| 2006/0106381 A1 | 5/2006 | Ferree et al. | |
| 2006/0106397 A1 | 5/2006 | Lins | |
| 2006/0136060 A1 | 6/2006 | Taylor | |
| 2006/0142760 A1 | 6/2006 | McDonnell | |
| 2006/0149230 A1 | 7/2006 | Kwak et al. | |
| 2006/0195102 A1 | 8/2006 | Malandain | |
| 2006/0217726 A1 | 9/2006 | Maxy et al. | |
| 2006/0240533 A1 | 10/2006 | Sengupta et al. | |
| 2006/0241610 A1 | 10/2006 | Lim et al. | |
| 2006/0271055 A1 | 11/2006 | Thramann | |
| 2007/0010822 A1 | 1/2007 | Zalenski et al. | |
| 2007/0073293 A1 | 3/2007 | Martz et al. | |
| 2007/0083200 A1 | 4/2007 | Gittings et al. | |
| 2007/0213829 A1 | 9/2007 | Le Couedic et al. | |
| 2007/0233096 A1 | 10/2007 | Garcia-Bengochea | |
| 2007/0270828 A1 | 11/2007 | Bruneau et al. | |
| 2007/0299445 A1 | 12/2007 | Shadduck et al. | |
| 2008/0009866 A1 | 1/2008 | Alamin et al. | |
| 2008/0021466 A1 | 1/2008 | Shadduck et al. | |
| 2008/0027435 A1 | 1/2008 | Zucherman et al. | |
| 2008/0033552 A1 | 2/2008 | Lee et al. | |
| 2008/0045949 A1 | 2/2008 | Hunt et al. | |
| 2008/0051784 A1 | 2/2008 | Gollogly | |
| 2008/0097431 A1 | 4/2008 | Vessa | |
| 2008/0108993 A1 | 5/2008 | Bennett et al. | |
| 2008/0114357 A1 | 5/2008 | Allard et al. | |
| 2008/0125780 A1 | 5/2008 | Ferree | |
| 2008/0177264 A1 | 7/2008 | Alamin et al. | |
| 2008/0177298 A1 | 7/2008 | Zucherman et al. | |
| 2008/0183209 A1 | 7/2008 | Robinson et al. | |
| 2008/0262549 A1 * | 10/2008 | Bennett et al. | 606/263 |
| 2008/0281423 A1 | 11/2008 | Sheffer et al. | |
| 2008/0312693 A1 | 12/2008 | Trautwein et al. | |
| 2008/0319487 A1 | 12/2008 | Fielding et al. | |
| 2009/0030457 A1 | 1/2009 | Janowski et al. | |
| 2009/0082820 A1 | 3/2009 | Fielding et al. | |
| 2009/0118766 A1 | 5/2009 | Park et al. | |
| 2009/0198282 A1 | 8/2009 | Fielding et al. | |
| 2009/0264929 A1 | 10/2009 | Alamin et al. | |
| 2009/0264932 A1 | 10/2009 | Alamin et al. | |
| 2009/0270918 A1 | 10/2009 | Attia et al. | |
| 2010/0004701 A1 | 1/2010 | Malandain et al. | |
| 2010/0023060 A1 | 1/2010 | Bennett et al. | |
| 2010/0036424 A1 | 2/2010 | Fielding et al. | |
| 2010/0234890 A1 | 9/2010 | Alamin et al. | |
| 2010/0249839 A1 | 9/2010 | Alamin et al. | |

FOREIGN PATENT DOCUMENTS

| | | |
|---|---|---|
| EP | 0743045 A3 | 12/1996 |
| EP | 1 994 901 A1 | 11/2008 |
| FR | 2 681 525 A1 | 3/1993 |
| FR | 2 714 591 | 7/1995 |
| FR | 2 717 675 A1 | 9/1995 |
| FR | 2 828 398 A1 | 2/2003 |
| FR | 2 851 154 | 8/2004 |
| FR | 2 874 167 A1 | 2/2006 |
| FR | 2 884 136 A1 | 10/2006 |
| WO | WO 01/28442 | 4/2001 |
| WO | WO 02/03882 A2 | 1/2002 |
| WO | WO 02/03882 A3 | 5/2002 |
| WO | WO 02/051326 | 7/2002 |
| WO | WO 02/071960 | 9/2002 |
| WO | WO 03/045262 | 6/2003 |
| WO | WO 03/045262 A3 | 1/2004 |
| WO | WO 2004/052246 | 6/2004 |
| WO | WO 2004/073532 | 9/2004 |
| WO | WO 2004/073533 | 9/2004 |
| WO | WO 2005/110258 A1 | 11/2005 |
| WO | WO 2008/051801 | 5/2008 |
| WO | WO 2008/051802 | 5/2008 |
| WO | WO 2008/051806 | 5/2008 |
| WO | WO 2008/051802 A3 | 7/2008 |
| WO | WO 2008/051806 A3 | 7/2008 |
| WO | WO 2008/051801 A3 | 8/2008 |
| WO | WO 2009/149407 | 12/2009 |
| WO | WO 2010/028165 | 3/2010 |
| WO | WO 2010/028165 A8 | 10/2010 |
| WO | WO 2009/149407 A9 | 2/2011 |

OTHER PUBLICATIONS

Abbott Spine, Wallis Surgical Technique [Product Brochure], 2006; 24 pages total.

Al Baz et al., "Modified Technique of Tension Band Wiring in Flexion Injuries of the Middle and Lower Cervical Spine," Spine, vol. 20, No. 11, 1995, p. 1241-1244.

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

Dickman et al., "Comparative Mechanical Properties of Spinal Cable and Wire Fixation Systems," Spine, vol. 22, No. 6, Mar. 15, 1997, pp. 596-604.

Frymoyer et al., "An Overview of the Incidence and Costs of Low Back Pain" Orthrop. Clin. North Am., 1991;22: 263-271.

Garner et al., "Development and Preclinical Testing of a New Tension-Band Device for the Spine: the Loop system," European Spine Journal, vol. 11 (Suppl 2), 2002, pp. S186-S191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

Leahy et al., "Design of Spinous Process Hooks for Flexible Fixation of the Lumbar Spine," Proceedings of the Institution of Mechanical Engineers, Part H, Journal of Engineering in Medicine, vol. 214, No. 5, Sep. 27, 2000, pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000, pp. 489-495.

Medtronic Sofamor Danek USA, Inc., Diam™ System Implant; 2006 [Product Brochure]; downloaded from the Internet: <http://spineinfo.ru/~files/DIAMST.pdf>, 20 pages total.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

Papp et al., "An In Vitro Study of the Miomechanical Effects of Flexible Stabilization on the Lumbar Spine," Spine, vol. 22, No. 2, Jan. 15, 1997, pp. 151-155.

Shepherd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville et al., "Ligamentoplastie Intervertebrale Avec Cale Souple dans Les Instabilities Lombaries" <<Intervertebral Ligamentoplasty with Flexible Wedge in Lumbar Instability, >>, Orthop Traumatol, vol. 2, 1992, pp. 259-264.

\* cited by examiner

SURGICAL TETHER APPARATUS AND METHODS OF USE

CROSS-REFERENCES TO RELATED APPLICATIONS

The present application is a non-provisional of, and claims the benefit of U.S. Provisional Patent Application No. 61/158,886 filed Mar. 10, 2009, the entire contents of which are incorporated herein by reference. The present application is also related to the U.S. Provisional Patent Application No. 61/158,892 filed Mar. 10, 2009, the entire contents of which is incorporated herein by reference.

BACKGROUND OF THE INVENTION

1. Field of the Invention

The present invention generally relates to medical methods and apparatus. More particularly, the present invention relates to methods and apparatus used to restrict flexion of a fused spinal segment. The methods and apparatus disclosed herein may be used alone or in combination with fusion or other orthopedic procedures intended to treat patients with spinal disorders such as back pain.

A host of spinal conditions exist which often result in instability issues and/or back pain. A major source of chronic low back pain is discogenic pain, also known as internal disc disruption. Discogenic pain can be quite disabling, and for some patients, can dramatically affect their ability to work and otherwise enjoy their lives. Patients suffering from discogenic pain tend to be young, otherwise healthy individuals who present with pain localized to the back. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards). Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. It would therefore be desirable to provide methods and apparatus that can be used alone or in combination with other spinal treatments to reduce loading in the area of the disc and adjacent tissue.

A number of treatments exist for addressing back pain and spinal instability. Some of these include, but are not limited to, fusion of the affected spinal segment. The patient may also be required to wear an external back brace for three to six months in order to allow the fusion to heal. Unfortunately, external braces are not always desirable since such braces can be uncomfortable, expensive, and inconvenient to use, and patient compliance often is low. An alternative to the back brace is to instrument the spinal segment with traditional instrumentation. Traditional instrumentation also facilitates fusion and prevents subsequent motion along the fused segment. While this treatment may be effective, it can also have shortcomings. For example, the fusion procedure with traditional instrumentation is more invasive, and when rigid instrumentation is used (e.g. pedicle screws and spinal stabilization rods), the instrumented region of the spinal segment becomes very stiff, and motion is prevented across the fusing segment. Loads can be borne by the instrumentation rather than the tissue, and loads and motion at adjacent segments can be increased. This is not always desirable, since a certain amount of motion and loading may actually help the healing process, promote fusion, and prevent excessive wear and tear on adjacent implants and tissue. Also, loading on the instrumentation may result in loosening or other mechanical failure of the instrumentation. Therefore, it would be desirable to have an improved device for instrumenting a fused spinal segment. It would also be desirable if an improved device minimized loads at the device/bone interface to minimize the potential of loosening and other mechanical failure. It would also be desirable if the device diminished the peak loading patterns at the bone/implant interface.

For the aforementioned reasons, it would therefore be advantageous to provide methods and apparatus that can be used with spinal fusion to help facilitate fusion of the vertebrae while still allowing some motion and loading of the fusion graft. It would be further desirable to provide methods and apparatus that are minimally invasive to the patient, cost effective and easy to use.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; 2005/0192581; 2005/0216017; US 2006/0069447; US 2006/0136060; US 2006/0240533; US 2007/0213829; US 2007/0233096; 2008/0009866; 2008/0108993; Published PCT Application Nos. WO 01/28442 A1; WO 02/03882 A2; WO 02/051326 A1; WO 02/071960 A1; WO 03/045262 A1; WO2004/052246 A1; WO 2004/073532 A1; WO2008/051806; WO2008/051423; WO2008/051801; WO2008/051802; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3: 319-323; Shepherd (2001) Medical Eng. Phys. 23, No. 2: 135-141; and Voydeville et al (1992) Orthop Traumatol 2:259-264.

BRIEF SUMMARY OF THE INVENTION

The present invention generally relates to medical methods and apparatus. More particularly, the present invention relates to methods and apparatus used to restrict flexion of a spinal segment to be fused. The methods and apparatus disclosed herein may be used alone or in combination with fusion or other orthopedic procedures intended to treat patients with spinal disorders such as back pain.

In a first aspect of the present invention, a method for controlling flexion in a spinal segment of a patient comprises performing a spinal fusion procedure on a pair of adjacent vertebrae in the spinal segment and implanting a constraint device into the patient. The step of implanting comprises coupling the constraint device with the spinal segment. The method also includes adjusting length or tension in the constraint device so that the constraint device provides a force resistant to flexion of the spinal segment undergoing fusion. The constraint device also modulates loads borne by the spinal segment undergoing fusion, including the bone grafting material and tissue adjacent thereto. In some embodiments, the constraint device may have an upper tether portion, a lower tether portion and a compliance member coupled therebetween. An upper portion of the constraint device may be engaged with a superior spinous process and a lower portion of the constraint device may be engaged with an inferior spinous process or a sacrum. The length or tension of the constraint device may be adjusted to a desired value. The length or tension may be adjusted to encourage the fusion to form in a position consistent with the natural lordotic curve of the patient.

The step of performing the spinal fusion procedure may comprise applying bone grafting material to at least one of posterior, lateral, posterolateral or interbody locations on the adjacent vertebrae. Bone graft may be placed between or alongside the spinous processes of the vertebrae to be fused, and to which the constraint is coupled. Sometimes performing the spinal fusion procedure may comprise intervertebral grafting in a disc space between the pair of adjacent vertebrae or applying bone grafting material to the superior spinous process and the inferior spinous process. Performing the spinal fusion procedure may also comprise implanting a first prosthesis into the patient. The first prosthesis may be engaged with at least a portion of the spinal segment. The constraint device may modulate loads borne by the first prosthesis or tissue adjacent thereto. The constraint device may be implanted and coupled with the spinal segment during the same surgical procedure as the fusion procedure. Additionally, the constraint device stabilizes the segment as it fuses together, which may take several months to form following the fusion procedure. After fusion has occurred, the constraint no longer provides any further benefit and it may be removed or left in place. If left in place, the constraint device may last longer than traditional instrumentation. Because of the compliance of the constraint device, it is able to accommodate micromotion in the fused segment and therefore the constraint device experiences lower loading and wear as compared to rigid instrumentation systems which transmit complex segmental loads and are more likely to fail in service.

In some embodiments, implanting the first prosthesis may comprise positioning an intervertebral device between the pair of adjacent vertebrae. The intervertebral device may be configured to maintain alignment and distance between the pair of adjacent vertebrae during arthrodesis. The intervertebral device may comprise an interbody fusion cage. In other embodiments, implanting the first prosthesis may comprise positioning bone grafting material between the pair of adjacent vertebrae and the bone grafting material may be selected from the group consisting of an allograft or an autograft of bone tissue, a xenograft and also synthetic bone graft material, or agents such as bone morphogenetic protein designed to stimulate bone growth. In addition to positioning bone grafting material, the step of implanting the first prosthesis may further comprise positioning an interbody fusion cage between the pair of adjacent vertebrae during the development of arthrodesis.

Implanting the constraint device may comprise engaging the constraint device with the superior spinous process and the inferior spinous process or sacrum without implanting a prosthesis directly in an interspinous region extending between an inferior surface of the superior spinous process and a superior surface of the inferior spinous process or sacrum. The step of implanting the constraint device may also comprise piercing an interspinous ligament to form a penetration superior to a superior surface of the superior spinous process and advancing the upper tether portion through the penetration. The tether may also be advanced through a gap between the superior spinous process and an adjacent spinous process that has been created by surgical removal of the interspinous ligament therefrom. Implanting the constraint device may also comprise piercing an interspinous ligament to form a penetration inferior to an inferior surface of the inferior spinous process and advancing the lower tether portion through the penetration. The tether may also be advanced through a gap between the inferior spinous process and an adjacent spinous process or a sacrum that has been created by surgical removal of the interspinous ligament therefrom. Alternatively, the constraint device may be advanced through a gap between the spinous processes created by surgical removal of an interspinous ligament.

Adjusting length or tension in the constraint device may comprise adjusting the length or tension a plurality of times during treatment of the spinal segment and during or after healing of the spinal segment. Adjustment may be performed transcutaneously.

Sometimes, at least one of the first prosthesis or the constraint device may comprise a therapeutic agent adapted to modify tissue in the spinal segment. The therapeutic agent may comprise a bone morphogenetic protein.

In another aspect of the present invention, a system for controlling flexion in a spinal segment of a patient comprises a constraint device disposed at least partially around a region of the spinal segment that is to be fused. The constraint device has an upper tether portion, a lower tether portion and a compliance member coupled therebetween. The upper tether portion is coupled with a superior spinous process along the spinal segment to be fused and the lower tether portion is coupled with an inferior spinous process or sacrum along the spinal segment to be fused. Length or tension in the constraint device is adjustable so that the constraint device provides a force resistant to flexion of the spinal segment undergoing fusion. Also, the constraint device modulates loads borne by the spinal segment to be fused including the graft material and tissue adjacent thereto.

The constraint device may be engaged with the superior spinous process and the inferior spinous process or sacrum and an interspinous region extending directly between an inferior surface of the superior spinous process and a superior surface of the inferior spinous process or sacrum may remain free of an implanted prosthesis.

The system may further comprise a first prosthesis coupled with the region of the spinal segment to be fused. The constraint device may modulate loads borne by the first prosthesis or by tissue adjacent thereto. Sometimes, the first prosthesis may comprise an intervertebral device disposed between two adjacent vertebrae in the region of the spinal segment to be fused. The intervertebral device may be configured to maintain alignment and distance between the two adjacent vertebrae after intervertebral disc material has been disposed between the two adjacent vertebrae during development of arthrodesis. The intervertebral device may comprise an interbody fusion cage that is adapted to facilitate fusion of the two adjacent vertebrae in the region of the spinal segment to be fused. The first prosthesis may also comprise bone grafting material disposed between two adjacent vertebrae where the bone grafting material is adapted to facilitate fusion of the two adjacent vertebrae in the spinal segment. The bone grafting material may be selected from the group consisting of an allograft, an autograft, a xenograft, a synthetic material and combinations thereof combination thereof.

These and other embodiments are described in further detail in the following description related to the appended drawing figures.

DETAILED DESCRIPTION OF THE INVENTION

Figure 1A:
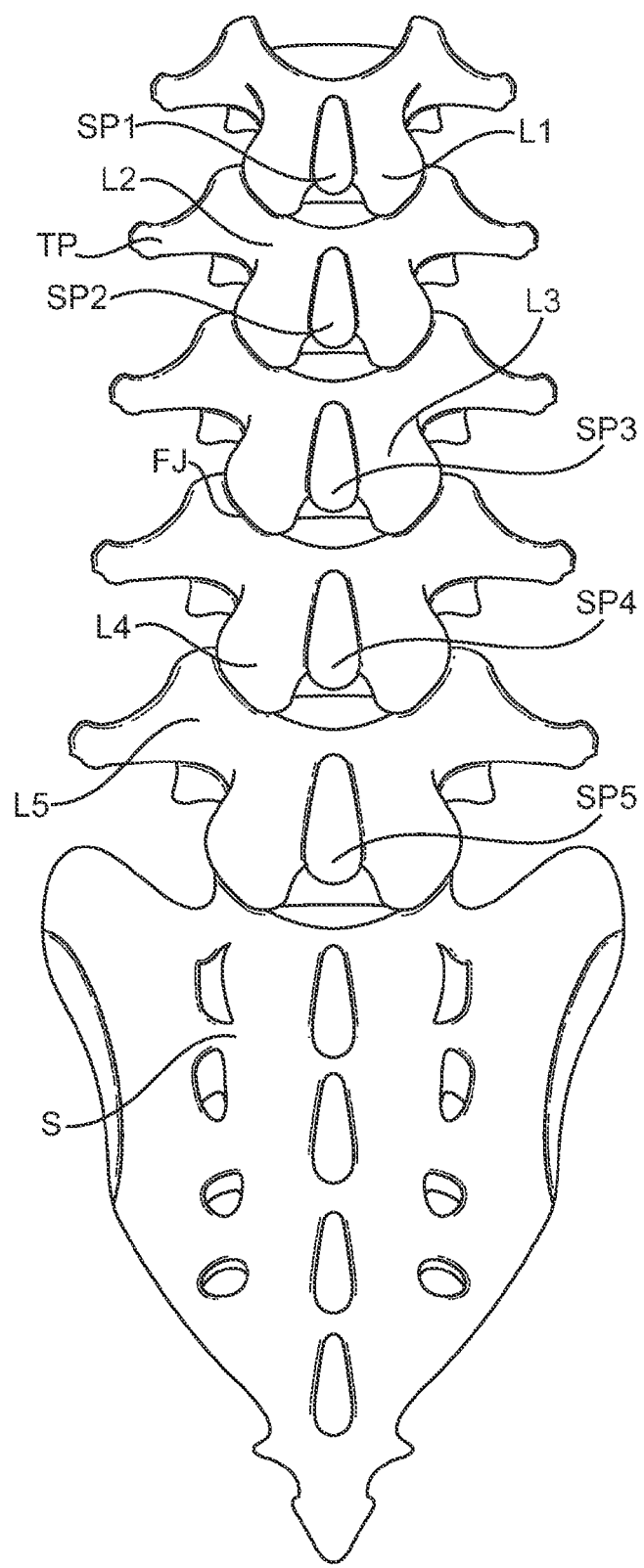
FIG. 1A is a schematic diagram illustrating the lumbar region of the spine.
Figure 1B:
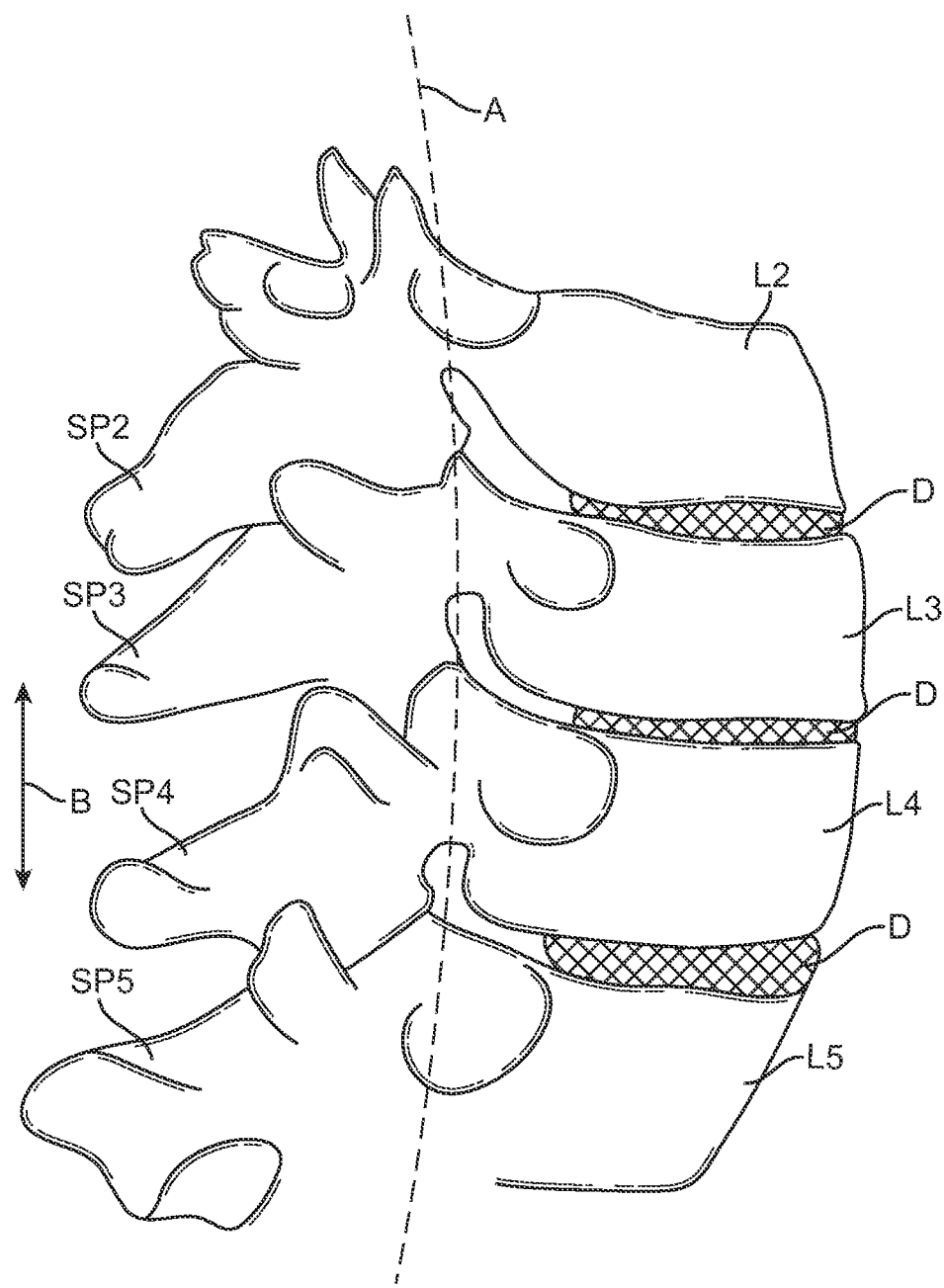
FIG. 1B a schematic illustration showing a portion of the lumbar region of the spine taken along a sagittal plane.

FIG. 1A is a schematic diagram illustrating the lumbar region of the spine including the spinous processes (SP), facet joints (FJ), lamina (L), transverse processes (TP), and sacrum (S). FIG. 1B is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the lumbar spine where the spine has a slight anterior convexity and slight posterior concavity. In some cases, the presence of the constraint of the present invention may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae in a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

A major source of chronic low back pain is discogenic pain, also known as internal disc disruption. Pain experienced by patients with discogenic low back pain can be thought of as flexion instability, and is related to flexion instability manifested in other conditions such as spondylolisthesis, a spinal condition in which abnormal segmental translation is exacerbated by segmental flexion. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards). Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. Patients with discogenic pain accommodate their syndrome by avoiding positions such as sitting, which cause their painful segment to go into flexion, preferring positions such as standing, which maintain their painful segment in extension.

Discogenic pain may be treated in a number of ways ranging from conservative treatments to surgery and implantation of prostheses. Conservative treatments include physical therapy, massage, anti-inflammatory and analgesic medications, muscle relaxants, and epidural steroid injections. These treatments have varying degrees of success and often patients typically continue to suffer with a significant degree of pain. Other patients elect to undergo spinal fusion surgery, which sometimes requires discectomy (removal of the disk) together with fusion of adjacent vertebra. Fusion may or may not also include instrumentation of the affected spinal segment including, for example, pedicle screws and stabilization rods, and/or intervertebral devices. Fusion is not lightly recommended for discogenic pain because it is irreversible, costly, associated with high morbidity, and has questionable effectiveness. Fusion is, however, still used for discogenic pain despite these drawbacks, and fusion is also used for many other spinal disorders related to pain and instability. While fusion with traditional instrumentation is promising, in some circumstances it may have drawbacks. Because most instrumentation is rigid or only provides limited motion, motion around the fused segment is prevented and loads can be fully borne by the instrumentation rather than the tissue. While prevention of significant motion is important during the fusion healing process, a certain amount of micromotion and loading of the tissue is desirable as this can promote fusion. Furthermore, allowing such motion and loading may enable the segment to fuse in a natural position, enabling maintenance of the lordotic curve in the treated region of the spine and avoiding the creation of kyphosis or "flat back" with fusion instrumentation. Therefore it would be desirable to provide a device that can stabilize a fused region like traditional instrumentation while still allowing some micromotion and loading in the fused region. Furthermore, loading along the spinal column may be modified due to the fusion and this may result in excessive loading on the fused region, adjacent tissue or devices used. It would therefore be desirable to provide methods and apparatus that can be used alone or in conjunction with spinal fusion or other spinal treatments that allow micromotion at the level of the fusion and that help to reduce the excessive loading and provide additional flexion stability.

Figure 2:
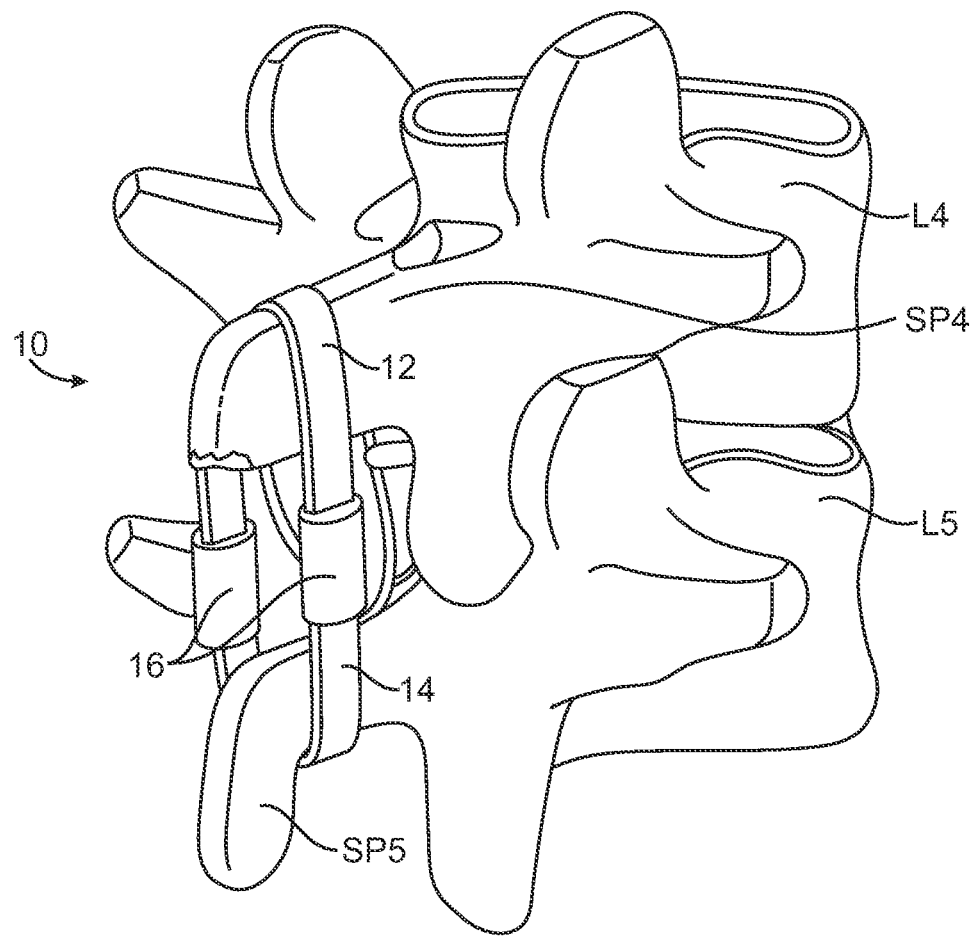
FIG. 2 illustrates a spinal implant of the type described in U.S. Patent Publication No. 2005/0216017A1.

FIG. 2 shows a spinal implant of the type described in related U.S. Patent Publication No. 2005/02161017 A1, now U.S. Pat. No. 7,458,981 the entire contents of which are incorporated herein by reference. The constraint device of FIG. 2 may be used alone or in combination with other spinal treatments to allow micromotion in a spinal segment that is fused or that is undergoing fusion, and to reduce loads borne by the region undergoing fusion or devices implanted into the patient as well as loads borne by adjacent tissue, thereby facilitating healing and reducing tissue damage and wear and tear. Furthermore, the constraint device may be used to provide greater stability to the spinal segment and to encourage the healing of the fusion at an intervertebral angle consistent with the lordotic curve of the patient.

As illustrated in FIG. 2, an implant 10 typically comprises a tether structure having an upper strap component 12 and a lower strap component 14 joined by a pair of compliance elements 16. A small aperture is pierced through the interspinous ligament (not illustrated) and the upper strap is passed through the aperture. The upper strap 12 may then be disposed over the top of the spinous process SP4 of L4. A similar lower aperture is pierced through the interspinous ligament allowing the lower strap 14 to extend over the bottom of the spinous process SP5 of L5. The compliance element 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which is a force that resists flexion. The force increases as the processes move further apart. Usually, the straps themselves will be essentially non-compliant so that the degree of elasticity or compliance may be controlled and provided solely by the compliance elements 16. Additional details on implant 10 and the methods of use are disclosed in International PCT Applications Nos. PCT/US2009/055914; PCT/US2009/046492; U.S. Provisional Patent Application Nos. 61/093,922; 61/059,543; 61/059,538; U.S. patent application Ser. No. 12/106,103; U.S. Patent Publication Nos. 2010/0023060; 2008/0262549; and U.S. Pat. No. 7,458,981; the entire contents, each of which is incorporated in its entirety herein by reference. The constraint device of FIG. 2 may be used along with fusion to provide better clinical outcomes than traditionally instrumented fusion procedures. Additionally, in some situations, it may be desirable to couple the constraint device with the sacrum rather than an inferior spinous process. Additional disclosure on sacral attachment may be found in U.S. Provisional Patent Application No. 61/149,224; International PCT Application PCT/US2010/022767; and U.S. patent application Ser. No. 11/827,980, the entire contents of which are incorporated herein by reference.

Figure 3A:
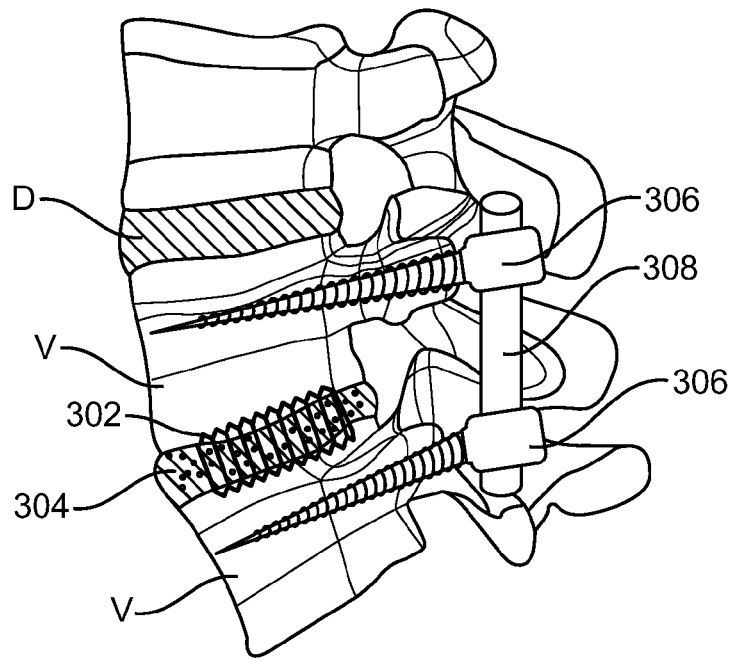
FIG. 3A illustrates an instrumented region of a fused spinal segment.
Figure 3B:
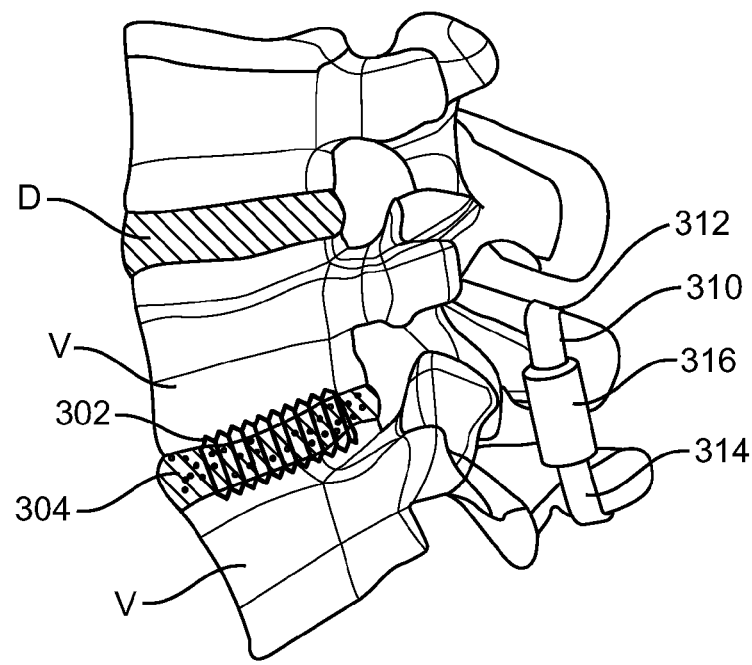
FIG. 3B illustrates the use of a constraint device in a fused region of a spinal segment.

FIG. 3A illustrates traditional fusion and instrumentation of a spinal segment. In FIG. 3A, the intervertebral disc D between adjacent vertebrae V has been removed and bone graft material 304 has been implanted therebetween. Optionally, a spinal fusion cage 304 is also implanted between the adjacent vertebrae in order to facilitate fusion between the vertebrae. The bone graft material may be an allograft or an autograft of bone material. Xenografts and synthetic graft material may also be used. Spinal fusion between the vertebral bodies (within the disc space) as described above is known as interbody fusion. Another common spinal fusion technique is posterolateral fusion, where the bone graft is applied between the transverse processes of the motion segment to be fused. The methods and systems described here are applicable to both fusion techniques. Once the bone grafting material and/or fusion cage have been implanted, the spinal segment is often instrumented with pedicle screws 306 and stabilization rods 308 in order to prevent motion around the fused region thereby promoting fusion. Often four pedicle screws (two on either side of the spinal segment midline) and two stabilization rods (one on either side of the midline) are used, although FIG. 3A only illustrates two pedicle screws and one spinal rod since it is a lateral view. Some of the problems and challenges of an instrumented fusion have been previously discussed above. FIG. 3B illustrates an alternative embodiment of fusing a spinal segment using a constraint device such as the one illustrated in FIG. 2.

In FIG. 3B, the spinal segment is fused in a similar fashion as previously described with respect to FIG. 3A above. An intervertebral disc D is removed from between adjacent vertebrae V and bone grafting material 304 is implanted along with an optional fusion cage 302. Instead of instrumenting the fused segment with pedicle screws and rigid spinal rods, a constraint device is attached to the fused region of the spinal segment. Here, constraint device 310 generally takes the same form as the constraint device of FIG. 2 above, although any of the constraint devices disclosed herein may also be used. The constraint device 310 has an upper tether portion 310, a lower tether portion 314 and a compliance member 316 coupled therebetween. The upper tether portion 310 is disposed around a superior surface of a superior spinous process and the lower tether portion 314 is disposed around an inferior surface of an inferior spinous process. The constraint device may be implanted and coupled with the spinal segment such that the interspinous region extending from an inferior surface of the superior spinous process and a superior surface of the inferior spinous process remains free of any implants such as spacers or other prostheses (although in some embodiments, bone graft may be implanted in this space). The length or tension of the constraint device may be adjusted in order to tighten the resulting loop in order to control how much force compliance member 316 provides against flexion of the spinal segment. Additionally, the spring constant of the compliance member may be selected based on desired operating characteristics. Thus, the constraint device 310 may be adjusted so that is provides enough resistance to flexion so that fusion can occur, while at the same time allowing some micromotion between the adjacent fused vertebrae in order to further promote fusion and the rate of fusion and to enable healing of the fusion at an intervertebral angle that preserves the patient's lordotic curve. The constraint device also allows dynamic loading of the bone grafting material and/or the bone-cage interface, further promoting fusion and the rate of fusion. It should also be appreciated that the same benefits may be derived when the graft is applied to the transverse processes (as in postero-lateral fusion), or the posterior elements of the fused vertebrae. Unlike traditional instrumentation where screws and rods unload the spine directly, using constraint device 310 helps unload the spine indirectly.

Figure 4B:
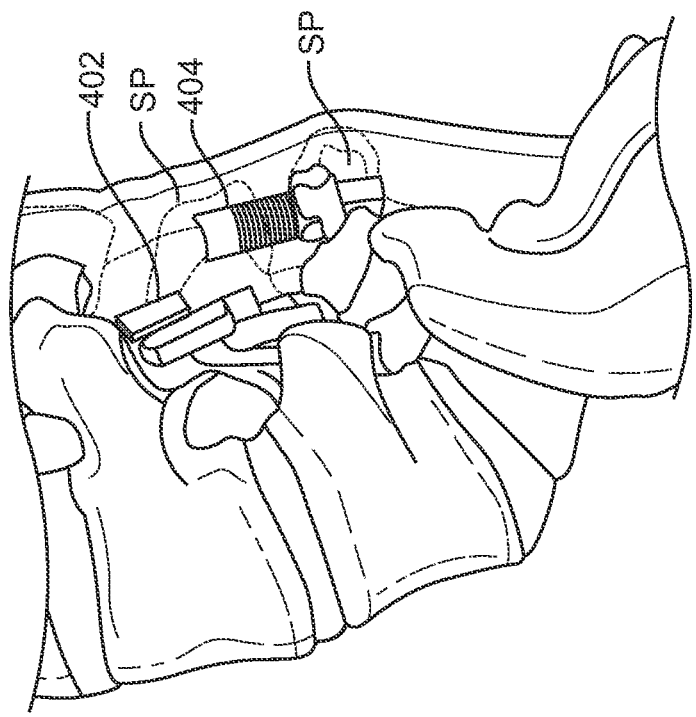
FIGS. 4B-4C illustrate the use of a constraint device along with fusion of the transverse processes.
Figure 4A:
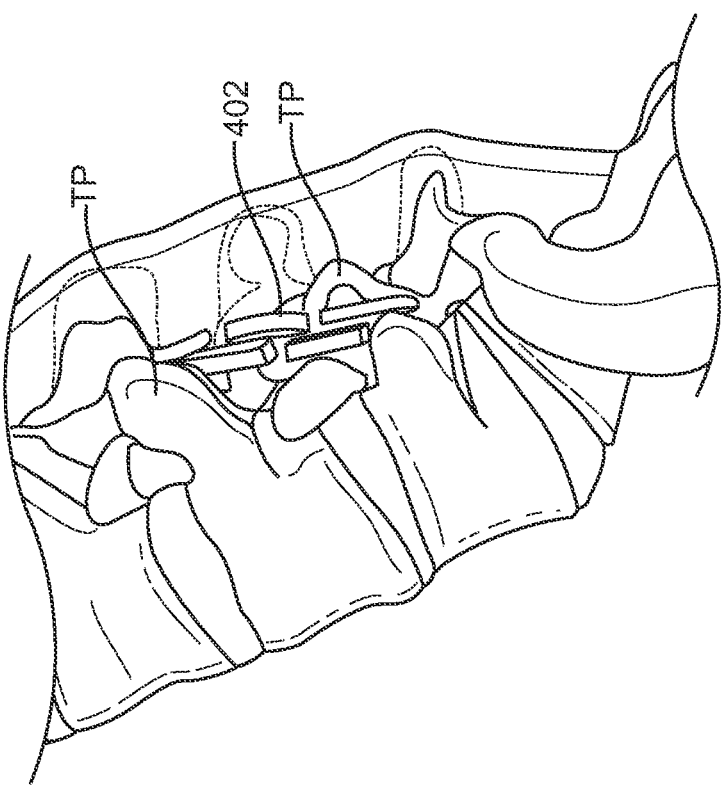
FIG. 4A illustrates fusion of the transverse processes.
Figure 4C:
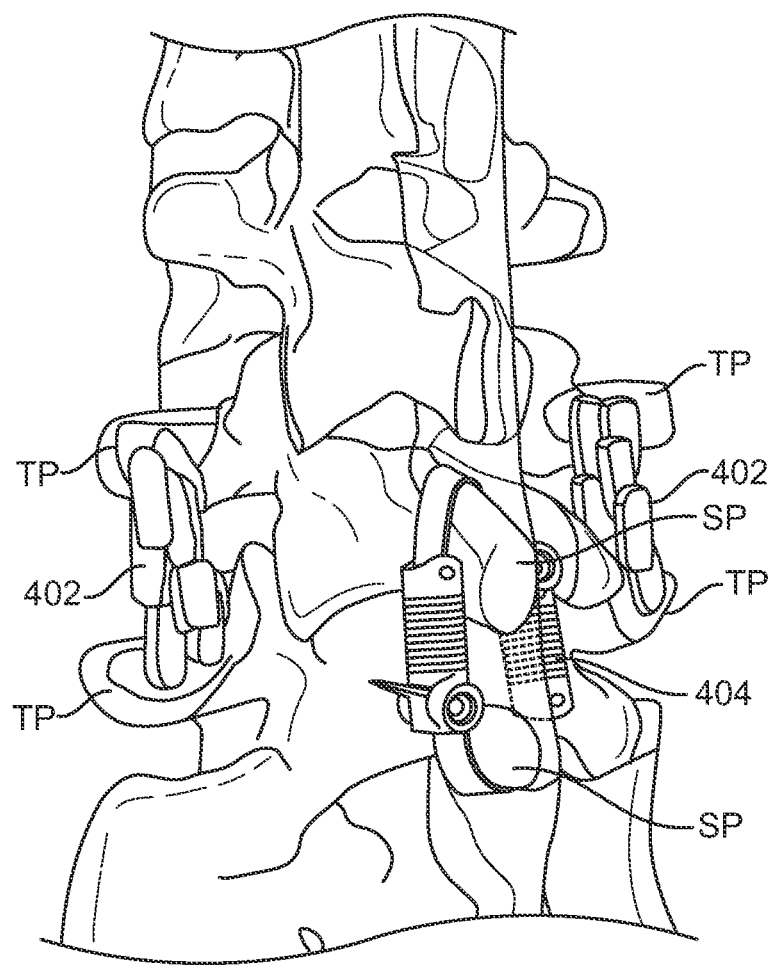

Spinal segment fusion may also be accomplished by fusing adjacent transverse processes. FIG. 4A illustrates bone graft 402 applied to the transverse processes TP, without any stabilizing instrumentation. This is known as an uninstrumented fusion. When the patient bends forward, the transverse processes move apart. This may disrupt the healing of the graft and result in non-union (pseudoarthrosis), or the fusion may heal in a flexed position (kyphosis). FIG. 4B illustrates use of a constraint device 404 engaged with the spinous processes SP, for resisting segmental flexion, so that the graft will heal and fusion will develop in a more natural lordosis posture. FIG. 4C is a posterior view of FIG. 4B that more clearly shows the fused regions and attachment of the constraint device. The constraint device 402 generally takes the same form as those described herein.

The present devices and methods are also advantageous over traditional instrumentation with screws and rods since the constraint device directly controls flexion and involves engagement of the facets more than pedicle screws and rods. This results in some indirect restriction of both axial rotation and sagittal translation, which may further help with the fusion and provide additional spinal segment stability. Another advantage of using the present devices and methods is that loading, other than tensile loading, is not transferred to the constraint device, and thus the constraint device is likely to experience fewer failure modes than traditional instrumentation in which all loading is transferred to the screws and rods. The present constraint device therefore, not only attempts to maximize therapeutic effectiveness, but also attempts to minimize failure, unlike most existing instrumentation devices which only attempt to maximize the therapy. The present device disclosed herein intentionally allows backward motion (extension) which helps avoid issues with extension loading and my help with balancing of the patient's vertebral column. Most other instrumentation devices or systems do not permit backward motion of the spinal segment.

Applying the constraint device as opposed to using traditional instrumentation techniques is also less invasive. A constraint device may be applied using minimally invasive techniques and does not require that screws be threaded into the pedicles. The constraint device is delivered through small incisions in the patient's back and the tether portions of the constraint device are passed through a small hole pierced in the interspinous ligament. Therefore, the procedure may be performed faster and with less blood loss and may require less operating room time than traditional instrumentation, resulting in a safer and more cost-effective procedure. Moreover, traditional instrumentation requires that tissue be resected, unlike the present method for implanting a constraint device which requires no resection at the affected level, e.g. no bone is required to be resected from the affected vertebral body or its posterior elements. Traditional instrumentation therefore may have more complications and safety concerns than a minimally invasive constraint device. The absence of screws and rods also frees up space in the patient's back, permitting easier access in case additional back surgery is required and also allowing other devices to be implanted in the area without the need to avoid interfering with screws and rods.

Additional disclosure on the methods and tools for implanting the constraint device are disclosed in greater detail in U.S. Patent Publication No. 2008/0262549; U.S. Provisional Patent Application No. 61/093,922; and International PCT Application No. PCT/US2009/055914; the entire contents of which were previously incorporated herein by reference. Additionally, several other length and tensioning adjustment mechanisms for a constraint device are disclosed in U.S. Provisional Patent Application Nos. 61/059,543; 61/059,538; U.S. Patent Publication No. 2010/0023060; International PCT Application No. PCT/US2009/046492; the entire contents of which were previously incorporated by reference.

Additional embodiments of constraint devices are also disclosed in U.S. patent application Ser. No. 12/106,103 and U.S. Pat. No. 7,458,981; the entire contents of which were previously incorporate herein by reference.

While the exemplary embodiments have been described in some detail for clarity of understanding and by way of example, a number of modifications, changes, and adaptations may be implemented and/or will be obvious to those skilled in the art. Hence, the scope of the present invention is limited solely by the independent claims.

What is claimed is:

1. A method for controlling flexion in a spinal segment of a patient, said method comprising:
    performing a spinal fusion procedure on a pair of adjacent vertebrae in the spinal segment, wherein the pair of adjacent vertebrae comprises a superior vertebra and an inferior vertebra, the superior vertebra having a spinous process with a superior surface and the inferior vertebra having a spinous process with an inferior surface;
    implanting a constraint device into the patient, wherein the step of implanting comprises coupling the constraint device with the spinal segment, wherein the constraint device comprises at least one compliance member and at least one tether, wherein the compliance member comprises an elastic member; and
    adjusting length or tension in the constraint device so that the constraint device provides an elastic force resistant to flexion of the fused spinal segment, and
    wherein the constraint device modulates loads borne by the fused spinal segment or tissue adjacent thereto, and
    wherein the at least one tether further comprises an upper tether portion and a lower tether portion, wherein the at least one compliance member is coupled therebetween, and
    wherein the step of coupling comprises engaging the upper tether portion with the superior surface and engaging the lower tether portion with the inferior surface or a sacrum.

2. The method of claim 1, wherein the length or tension is adjusted to a desired value.

3. The method of claim 1, wherein the length or tension is adjusted to encourage the fusion to form in a position consistent with the natural lordotic curve of the patient.

4. The method of claim 1, wherein the step of performing the spinal fusion procedure comprises at least one of posterior or lateral grafting of the adjacent vertebrae.

5. The method of claim 1, wherein the step of performing the spinal fusion procedure comprises posterolateral grafting of the adjacent vertebrae.

6. The method of claim 1, wherein the step of performing the spinal fusion procedure comprises intervertebral grafting in a disc space between the pair of adjacent vertebrae.

7. The method of claim 6, wherein intervertebral grafting comprises applying bone grafting material to a superior spinous process and an inferior spinous process.

8. The method of claim 1, wherein the step of performing the spinal fusion procedure comprises implanting a first prosthesis into the patient, the first prosthesis engaged with at least a portion of the spinal segment, wherein the constraint device modulates loads borne by the first prosthesis or tissue adjacent thereto.

9. The method of claim 8, wherein implanting the first prosthesis comprises positioning an intervertebral device between the pair of adjacent vertebrae, the intervertebral device configured to maintain alignment and distance between the pair of adjacent vertebrae during the development of arthrodesis.

10. The method of claim 9, wherein the intervertebral device comprises an interbody fusion cage.

11. The method of claim 8, wherein implanting the first prosthesis comprises positioning bone grafting material between the pair of adjacent vertebrae.

12. The method of claim 11, wherein implanting the first prosthesis further comprises positioning an interbody fusion cage between the pair of adjacent vertebrae, the fusion cage configured to maintain alignment and distance between the pair of adjacent vertebrae during the development of arthrodesis.

13. The method of claim 11, wherein the bone grafting material is selected from the group consisting of an allograft, an autograft, a synthetic graft and a xenograft.

14. The method of claim 8, wherein the first prosthesis or the constraint device comprises a therapeutic agent adapted to modify tissue in the spinal segment.

15. The method of claim 14, wherein the therapeutic agent comprises a bone morphogenetic protein.

16. The method of claim 1, wherein implanting the constraint device comprises engaging the constraint device with the superior spinous process and the inferior spinous process or sacrum without implanting a prosthesis directly in an interspinous region extending between an inferior surface of the superior spinous process and a superior surface of the inferior spinous process or the sacrum.

17. The method of claim 1, wherein the step of implanting the constraint device comprises:
    piercing an interspinous ligament to form a penetration superior to a superior surface of the superior spinous process; and
    advancing the upper tether portion through the penetration.

18. The method of claim 1, wherein the step of implanting the constraint device comprises:
    advancing the upper tether portion through a gap between the superior spinous process and an adjacent spinous process created by surgical removal of an interspinous ligament therefrom.

19. The method of claim 1, wherein the step of implanting the constraint device comprises:
    piercing an interspinous ligament to form a penetration inferior to the inferior surface of the inferior spinous process; and
    advancing the lower tether portion through the penetration.

20. The method of claim 1, wherein the step of implanting the constraint device comprises:
    advancing the lower tether portion through a gap between the inferior spinous process and an adjacent spinous process or a sacrum, the gap created by surgical removal of an interspinous ligament therefrom.

21. The method of claim 1, wherein adjusting length or tension in the constraint device comprises adjusting the length or tension a plurality of times during treatment of the spinal segment and during or after healing of the spinal segment.

22. The method of claim 21, wherein the step of adjusting comprises transcutaneously adjusting the length or tension.

23. The method of claim 1, wherein the constraint device is adjusted so that the force resistant to flexion is enough so that fusion can occur between the pair of adjacent vertebrae while allowing micromotion between the pair of adjacent vertebrae.

24. The method of claim 1, further comprising allowing extension of the spinal segment.

25. The method of claim 1, wherein the at least one tether is non-compliant.

* * * * *